(12) United States Patent
Tajima

(10) Patent No.: US 9,848,845 B2
(45) Date of Patent: Dec. 26, 2017

(54) RADIATION IMAGE DETECTING DEVICE

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 311 days.

(21) Appl. No.: 14/659,763

(22) Filed: Mar. 17, 2015

(65) Prior Publication Data

US 2015/0182182 A1   Jul. 2, 2015

Related U.S. Application Data

(63) Continuation of application No. PCT/JP2013/073287, filed on Aug. 30, 2013.

(30) Foreign Application Priority Data

Sep. 18, 2012 (JP) ................. 2012-204239

(51) Int. Cl.
  *A61B 6/00* (2006.01)
  *H04N 5/32* (2006.01)

(52) U.S. Cl.
  CPC ............ *A61B 6/542* (2013.01); *A61B 6/4283* (2013.01); *H04N 5/32* (2013.01); *A61B 6/4208* (2013.01); *A61B 6/469* (2013.01); *A61B 6/544* (2013.01)

(58) Field of Classification Search
  CPC ......... A61B 6/469; A61B 6/542; A61B 6/544; A61B 6/4208; A61B 6/4283
  See application file for complete search history.

(56) References Cited

U.S. PATENT DOCUMENTS

| 2004/0136498 | A1* | 7/2004 | Omernick | ................ H05G 1/30 378/109 |
| 2009/0161816 | A1* | 6/2009 | De Man | ................ A61B 6/032 378/9 |
| 2011/0180717 | A1 | 7/2011 | Okada | |
| 2013/0228694 | A1* | 9/2013 | Nakatsugawa | ...... A61B 6/4233 250/370.09 |

FOREIGN PATENT DOCUMENTS

JP   2008132216 A   *   6/2008
WO   WO 2012/056949 A1   5/2012

OTHER PUBLICATIONS

Japanese Office Action, dated Jul. 29, 2015, for Japanese Application No. 2012-204239, with an English translation thereof.
International Search Report issued in PCT/JP2013/073287 dated Nov. 5, 2013.
Written Opinion of the International Searching Authority issued in PCT/JP2013/073287 dated Nov. 5, 2013.

* cited by examiner

*Primary Examiner* — Glen Kao
(74) *Attorney, Agent, or Firm* — Birch, Stewart, Kolasch & Birch, LLP

(57) ABSTRACT

A sensor panel of an electronic cassette includes detection pixels each for outputting a dose signal corresponding to a dose of X-rays, an irradiation start judging section for judging whether or not X-ray irradiation has been started based on the dose signal, and an AEC section for judging whether or not an accumulated dose of X-rays has reached a target dose based on the dose signal. A gain setting section sets a gain of an integration amplifier in the case of using the irradiation start judging section lower than that in the case of using the AEC section.

11 Claims, 13 Drawing Sheets

FIG.6

| BODY PART TO BE IMAGED | TUBE VOLTAGE (kV) | TUBE CURRENT (mA) | IRRADIATION TIME (s) | DOSE MEASUREMENT FIELD | IRRADIATION STOP THRESHOLD VALUE |
|---|---|---|---|---|---|
| ... | ... | ... | ... | ... | ... |
| CHEST AP | V1 | I1 | T1 | ▫▫ | th1 |
| CHEST PA | V2 | I2 | T2 | ▫▫ | th2 |
| ... | ... | ... | ... | ... | ... |

~70

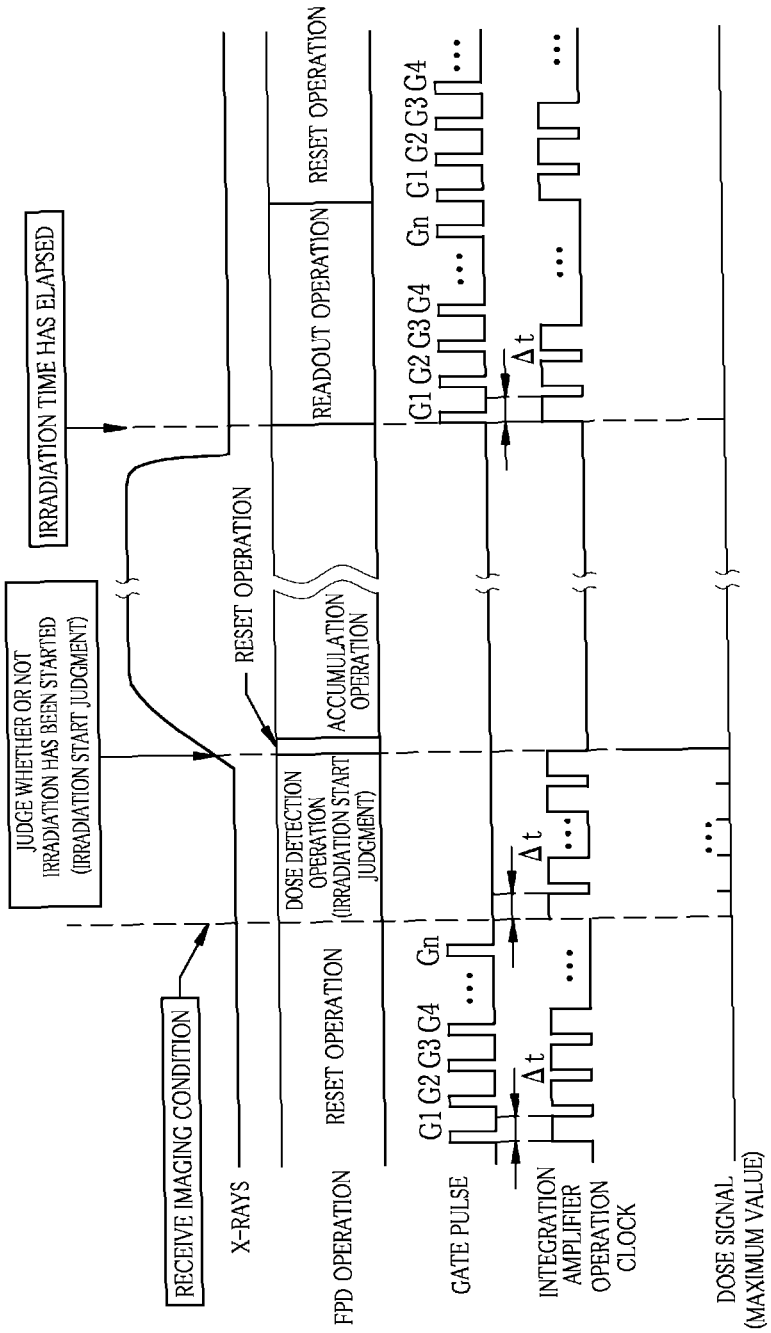

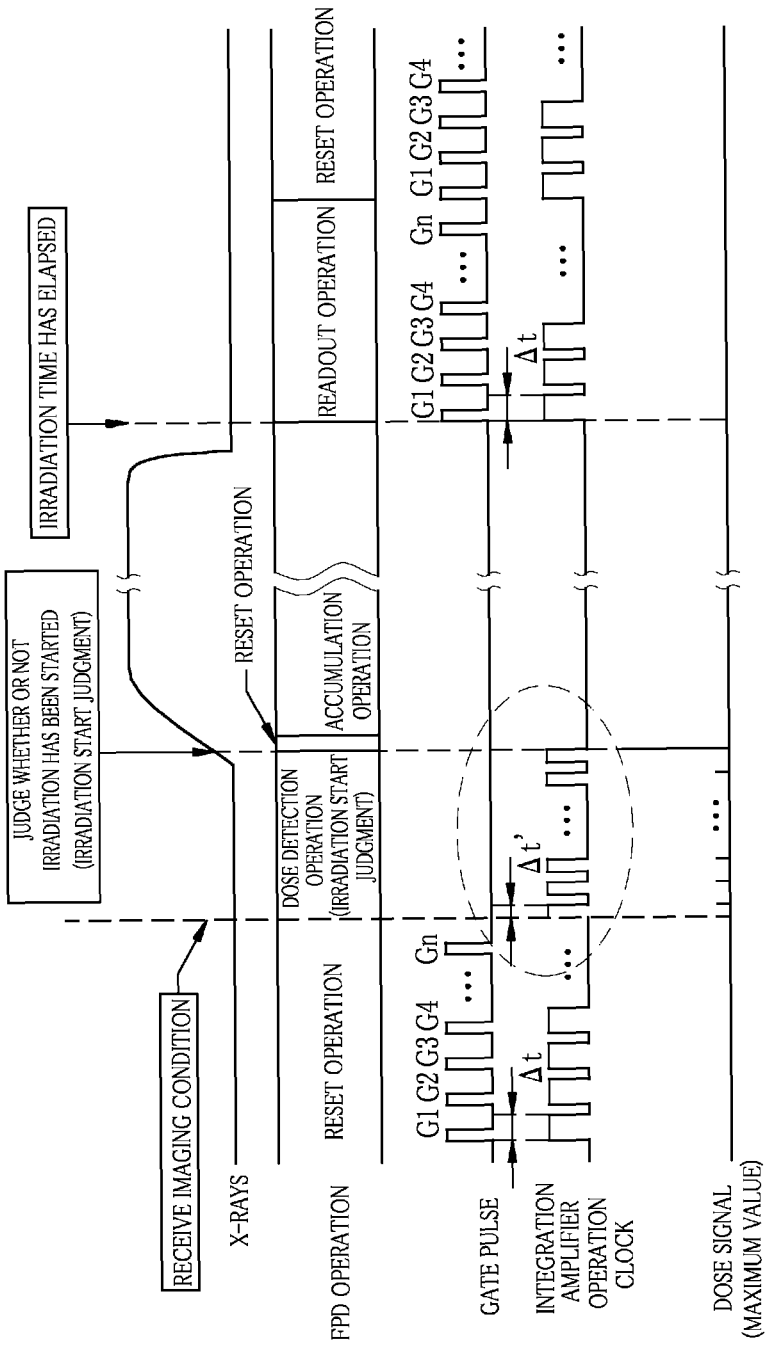

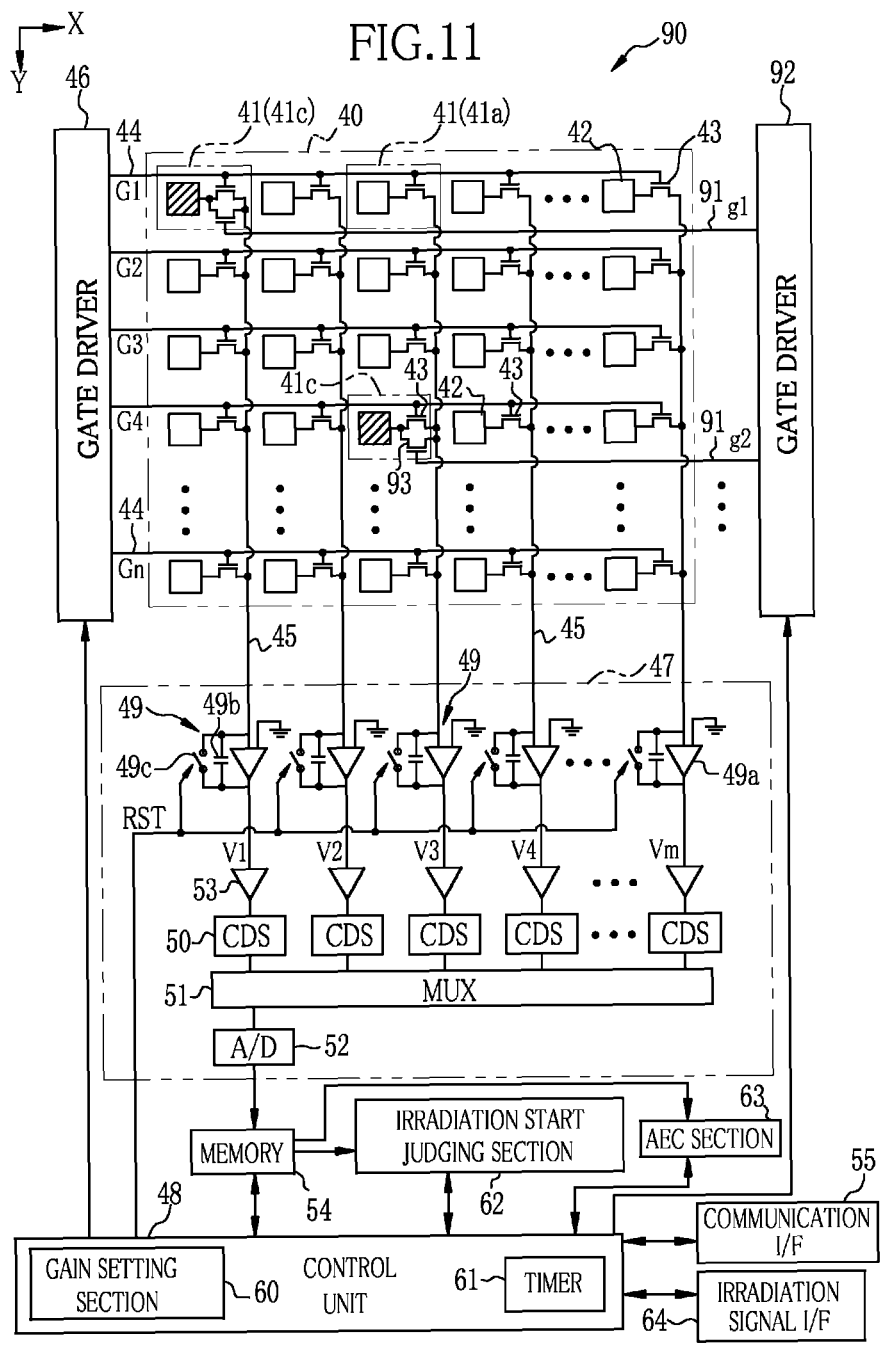

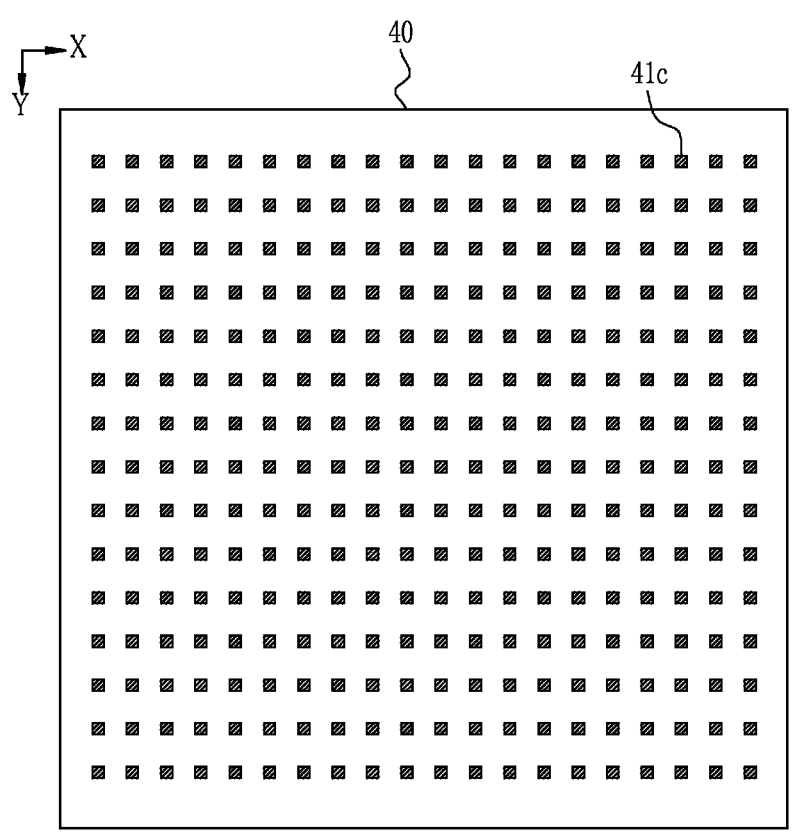

RADIATION IMAGE DETECTING DEVICE

CROSS-REFERENCE TO RELATED APPLICATIONS

This application is a Continuation of PCT International Application No. PCT/JP2013/073287 filed on Aug. 30, 2013, which claims priority under 35 U.S.C §119(a) to Japanese Patent Application No. 2012-204239 filed Sep. 18, 2012. The above application is hereby expressly incorporated by reference, in its entirety, into the present application.

BACKGROUND OF THE INVENTION

1. Field of the Invention

The present invention relates to a radiation image detecting device for detecting a radiation image.

2. Description Related to the Prior Art

In a medical field, an X-ray imaging system using radiation such as X-rays is known. The X-ray imaging system includes an X-ray generating apparatus for generating X-rays and an X-ray imaging apparatus for acquiring an X-ray image of an object (i.e. patient) from the X-rays having passed through the object. The X-ray generating apparatus includes an X-ray source for irradiating the X-rays to the object, a source controller for controlling operation of the X-ray source, and an irradiation switch for inputting a command to actuate the X-ray source to the source controller. The X-ray imaging apparatus includes an X-ray image detecting device for detecting the X-ray image by converting the X-rays having passed through the object into an electrical signal, and a console for controlling operation of the X-ray image detecting device and storing and displaying the X-ray image.

An X-ray imaging apparatus using an X-ray image detecting device for electronically detecting an X-ray image has been widely spread instead of an X-ray image recording device using an X-ray film or an imaging plate (IP) cassette. The X-ray image detecting device has a sensor panel that is also referred to as a flat panel detector (FPD). The sensor panel has an imaging area in which a plurality of pixels each for accumulating signal charges corresponding to a dose of incident X-rays are arranged in a matrix. Each of the pixels has a photoelectric converter for generating electric charges and accumulating the generated electric charges, and a switching element such as a thin film transistor (TFT). The sensor panel reads out the signal charges accumulated in the photoelectric converter of each of the pixels through a signal line disposed for each column of the pixels to a signal processing circuit upon turning-on of the switching element. The signal charges are converted into a voltage signal in the signal processing circuit. Thereby, an X-ray image is electronically detected.

In the X-ray image detecting device using the sensor panel, a reset operation is periodically carried out by the sensor panel for the purpose of discharging unnecessary electric charges from the pixels so as to minimize influence of noise of dark current added to the X-ray image. Accordingly, in the X-ray imaging system including the X-ray image detecting device using the sensor panel, the timing to start X-ray irradiation is synchronized with the timing for the sensor panel to finish the reset operation and start an accumulation operation for accumulating the signal charges in the pixels. For example, the source controller and the X-ray image detecting device are respectively provided with an interface (I/F) to establish intercommunication therebetween. The source controller transmits a synchronizing signal to the X-ray image detecting device in accordance with the timing to start X-ray irradiation. Upon receiving the synchronizing signal, the X-ray image detecting device makes the sensor panel shift to the accumulation operation. Alternatively, there is the following X-ray image detecting device having a function of judging whether or not X-ray irradiation has been started. The X-ray image detecting device is not connected to the source controller, and does not exchange any synchronizing signal with the source controller. Instead, the X-ray image detecting device detects the X-ray dose by a dose detection sensor, compares the detected X-ray dose with a predetermined irradiation start threshold value, and judges that the X-ray irradiation has been started when the detected X-ray dose exceeds the irradiation start threshold value. Then, the X-ray image detecting device makes the sensor panel start the accumulation operation.

Further, in some cases, an automatic exposure control (AEC) is performed in the X-ray imaging system. According to the AEC, in order to not only obtain an X-ray image having an appropriate image quality but also reduce X-ray exposure to an object, the X-ray dose is detected by a dose detection sensor during the X-ray imaging (during the X-ray irradiation), and the X-ray irradiation from the X-ray source is stopped when an integrated value of the dose (accumulated dose) reaches a target dose. The dose of X-rays irradiated from the X-ray source is determined by a tube current-time product (mAs value) as a product of X-ray irradiation time and a tube current for defining the dose of X-rays irradiated from the X-ray source per unit time. There are approximate recommended values for the items of imaging conditions including the irradiation time and the tube current depending on a body part of the object to be imaged (such as chest and head), the sex and age of the object, and the like. However, since X-ray transmittance is varied depending on an individual difference such as body frame of the object, the AEC is performed to achieve more appropriate image quality.

Conventionally, an ion chamber or the like has been used as a dose detection sensor. However, recently, there is proposed a technique of subjecting pixels in a sensor panel to simple modification such that the pixels serve as dose detection sensors. According to United States Patent Application Publication No. 2011/0180717 (corresponding to Japanese Patent Laid-Open Publication No. 2011-174908), some of pixels are used as dose detection sensors. Each of the pixels used as the dose detection sensor (hereinafter referred to as detection pixel) is connected to the wiring for radiation detection without through a switching element. Therefore, irrespective of whether the switching element is turned on or turned off, an output corresponding to the electric charges generated in the detection pixel (hereinafter referred to as dose signal) flow into the wiring for radiation detection. The dose signal is sampled at a predetermined cycle in a signal processing circuit to which the wiring for radiation detection is connected. Then, the dose signal is inputted to a control section. In the control section, based on the dose signal, the judgment on whether or not the X-ray irradiation has been started, or the AEC is performed. The signal processing circuit has an amplifier so as to amplify the dose signal flowing from the wiring for radiation detection at the time of judging whether or not the X-ray irradiation has been started, and outputs the amplified dose signal to the control section.

According to an irradiation profile representing change in the dose of X-rays per unit of time with the passage of time, there is a rising period during which the dose of X-rays gradually increases immediately after the start of X-ray irradiation. After the rising period, the dose of X-rays achieves a value corresponding to a tube current set by the imaging condition, and then the X-ray irradiation is continued at the dose of X-rays in a stationary period. During the AEC, the sampling operation of the dose signal is continued in the stationary period, and the accumulated dose is compared with the target dose based on the sampled dose signal, so as to determine the timing to stop the X-ray irradiation.

In contrast, the judgment on whether or not the X-ray irradiation has been started is required to be made promptly in order to minimize waste of the irradiated X-rays. Therefore, it is late to judge whether or not the X-ray irradiation has been started after the stationary period starts, and it is necessary to judge whether or not the X-ray irradiation has been started based on the dose signal which has been sampled during the rising period. Namely, the sampling period of the dose signal in the case of judging whether or not the X-ray irradiation has been started is much shorter than the sampling period of the dose signal in the case of performing the AEC.

It is known that random noise is generated in an analog signal processing circuit for reading out a dose signal. With regard to the random noise, there are random noise as positive components for increasing a signal value of the dose signal, and random noise as negative components for decreasing the signal value of the dose signal. In the AEC, the random noise as the positive components and the random noise as the negative components cancel each other in the course of integrating the dose signals obtained plural times in the sampling period longer than the sampling period of the dose signal in the case of judging whether or not the X-ray irradiation has been started. As a result, the noise components in the amplification gain at the time of reading out the dose signal are cancelled out, and thus the amplification gain contributes to only the amplification of the signal components. Consequently, as the gain is higher, the dose signal having a higher signal-noise ratio (S/N ratio) can be obtained, and the AEC can be performed at high precision.

In contrast, in the case where the judgment on whether or not the X-ray irradiation has been started is made, the sampling period of the dose signal is short. Therefore, the degree of cancellation between the positive components and the negative components in the random noise is smaller in comparison with the case where the AEC is performed. Accordingly, in the case where the gain to be applied to the dose signal is set to be equal to or higher than that in the case of performing the AEC, the random noise becomes large, and the S/N ratio of the dose signal is decreased in some cases. The problem becomes more serious as the sampling period is made shorter for the purpose of ensuring promptness in the judgment on whether or not the X-ray irradiation has been started. In the case where the sampling period is made shorter, the dose signal obtained at the first sampling is compared with the irradiation start threshold value in an extreme example, and the size of the random noise directly affects the S/N ratio of the dose signal. In the case where the judgment on whether or not the X-ray irradiation has been started is made in a state that the S/N ratio of the dose signal is poor, the probability of erroneous judgment on whether or not the X-ray irradiation has been started naturally becomes high.

SUMMARY OF THE INVENTION

In view of the foregoing, an object of the present invention is to provide a radiation image detecting device capable of judging whether or not radiation irradiation has been started more accurately.

To achieve the above and other objects of the present invention, a radiation image detecting device of the present invention includes a sensor panel, a dose detection sensor, an amplifier, an irradiation start judging section, an AEC section, and a control unit. The sensor panel has an imaging area on which pixels are arranged. Each of the pixels accumulates electric charges and outputs the electric charges to a signal line. The electric charges corresponds to a dose of radiation having been irradiated from a radiation source and having passed through an object. The dose detection sensor outputs a dose signal corresponding to the dose of radiation. The amplifier amplifies the dose signal. The irradiation start judging section judges whether or not radiation irradiation has been started based on the dose signal amplified by the amplifier. The AEC section judges whether or not an accumulated dose of radiation has reached a target dose based on the dose signal amplified by the amplifier. The control unit sets a gain of the amplifier at the time of judging whether or not radiation irradiation has been started by the irradiation start judging section lower than a gain of the amplifier at the time of judging whether or not the accumulated dose of radiation has reached the target dose by the AEC section.

The control unit preferably changes the gain in accordance with at least one of tube current set in the source controller and a thickness of the object.

The control unit preferably sets a sampling period of the dose signal at the time of judging whether or not radiation irradiation has been started by the irradiation start judging section shorter than a sampling period of the dose signal at the time of judging whether or not the accumulated dose of radiation has reached the target dose by the AEC section.

The control unit preferably changes a sampling period of the dose signal in accordance with at least one of tube current set in the source controller and a thickness of the object.

Preferably, a plurality of the dose detection sensors are arranged in the imaging area. Additionally, the dose detection sensors, from which each of the irradiation start judging section and the AEC section obtains the dose signal, are preferably selected from a plurality of the dose detection sensors.

Preferably, the dose detection sensors distributed in an entire surface of the imaging area are selected, and based on the dose signals from the selected dose detection sensors, the irradiation start judging section judges whether or not radiation irradiation has been started. Further, preferably, the dose detection sensors arranged in a portion of the imaging area corresponding to a region of interest which is the most remarkable in diagnosis are selected, and based on the dose signals from the selected dose detection sensors, the AEC section judges whether or not the accumulated dose of radiation has reached the target dose.

It is preferable that the dose detection sensors to be used for the judgment are selected in accordance with at least one of tube current set in the source controller and a thickness of the object.

The dose detection sensors are preferably equivalent to part of the pixels. For example, as the pixels, there are normal pixels each for accumulating signal charges upon receiving radiation and outputting the signal charges to the signal line in response to actuation of a switching element, and detection pixels directly connected to the signal line by a short-circuit line or directly connected to the signal line without through the switching element. Each of the detection pixels is used as the dose detection sensor. Detection pixels, each of which is driven separately from the normal pixels and provided with a switching element, also may be used as the dose detection sensor.

The sensor panel is preferably an electronic cassette contained in a portable housing.

According to the present invention, since the gain of the amplifier for amplifying the dose signal from the dose detection sensor at the time of judging whether or not radiation irradiation has been started by the irradiation start judging section lower than a gain of the amplifier at the time of judging whether or not the accumulated dose of radiation has reached a target dose by the AEC section. Therefore, it is possible to judge whether or not radiation irradiation has been started more accurately.

BRIEF DESCRIPTION OF DRAWINGS

For more complete understanding of the present invention, and the advantage thereof, reference is now made to the subsequent descriptions taken in conjunction with the accompanying drawings, in which:

FIG. 6 is a table showing imaging conditions;

FIG. 9 is a view showing a shift in operation of a sensor panel in the case where an irradiation start judging section is used;

FIG. 10 is a view showing a shift in operation of the sensor panel in the case where a sampling period of a dose signal is made short at the time of judging whether or not irradiation has been started;

FIG. 11 is a block diagram showing an internal structure of an electronic cassette according to another embodiment;

FIG. 12 a view showing arrangement of detection pixels according to another embodiment;

DESCRIPTION OF THE PREFERRED EMBODIMENTS

First Embodiment

Figure 1:
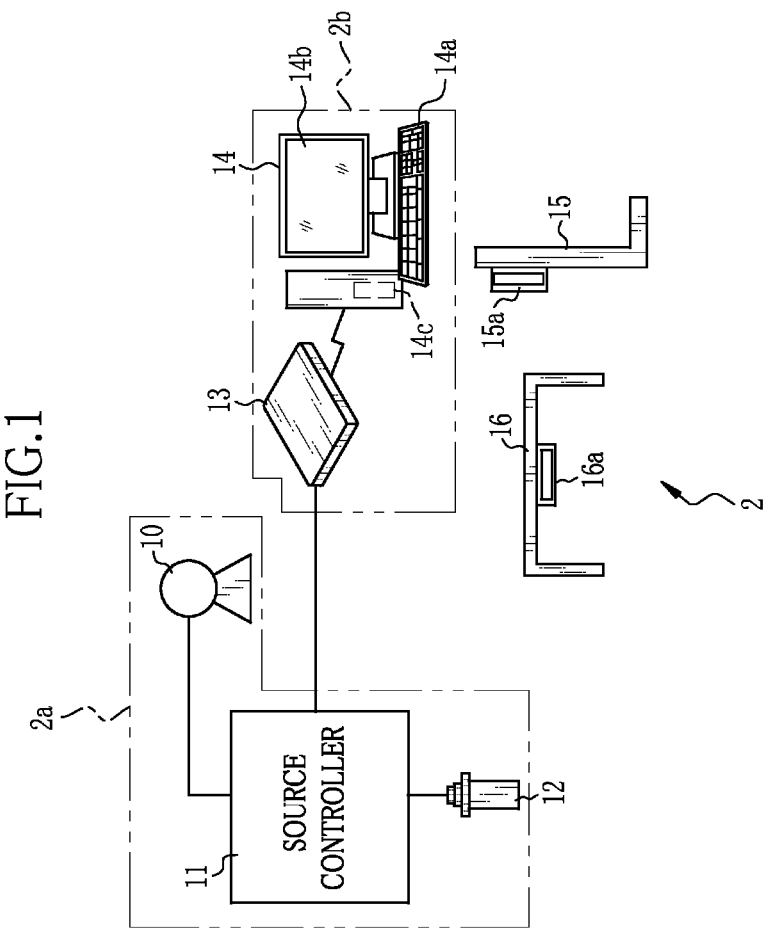
FIG. 1 is a schematic view showing an X-ray imaging system.

In FIG. 1, an X-ray imaging system 2 of the present invention includes an X-ray source 10, a source controller 11 for controlling operation of the X-ray source 10, an irradiation switch 12 for giving a command to start warming-up and X-ray irradiation to the X-ray source 10, an electronic cassette 13 having a function of judging whether or not radiation irradiation has been started and an automatic exposure control (AEC) function of stopping the radiation irradiation when an accumulated dose of radiation reaches a target dose so as to detect X-rays having passed through an object (i.e. patient) and output an X-ray image, a console 14 for performing operation control of the electronic cassette 13 and performing display processing of the X-ray images, an upright-posture imaging table 15 for imaging the object in a standing posture, and a supine-posture imaging table 16 for imaging the object in a lying posture. The X-ray source 10, the source controller 11, and the irradiation switch 12 constitute an X-ray generating apparatus 2a. The electronic cassette 13 and the console 14 constitute an X-ray imaging apparatus 2b. Additionally, a source moving device (not shown in the drawing) is provided to set the X-ray source 10 in a desired direction and at a desired position. The X-ray source 10 is shared between the upright-posture imaging table 15 and the supine-posture imaging table 16.

The X-ray source 10 has an X-ray tube and an irradiation field limiter (collimator) for limiting an irradiation field of the X-rays to be irradiated from the X-ray tube. The X-ray tube has a cathode composed of a filament for emitting thermal electrons, and an anode (target) for irradiating the X-rays upon collision with the thermal electrons emitted from the cathode. Upon receiving a command to start the warming-up of the X-ray source 10, the anode starts rotating. After the anode rotates by the prescribed number of rotations, the warming-up of the X-ray source 10 is finished. The irradiation field limiter is composed of, for example, four lead plates for shielding the X-rays disposed on each side of a quadrangle, such that a quadrangular irradiation opening through which the X-rays pass is formed in the middle thereof. Shifting of the positions of the lead plates varies the size of the irradiation opening so as to limit the irradiation field.

The console 14 is communicably connected to the electronic cassette 13 in a wired manner or a wireless manner, and controls the operation of the electronic cassette 13 in response to input operation by an operator through an input device 14a such as a keyboard. The X-ray image transmitted from the electronic cassette 13 is displayed on the monitor 14b of the console 14, and further, the data thereof is stored in a data storage. The data storage is, for example, a storage device 14c such as a hard disk or a memory in the console 14, or an image storage server connected to the console 14 through a network.

The console 14 receives the input of an examination order containing information relating to the sex, age, body part to be imaged, and imaging objective of each object, and displays the examination order on the monitor 14b. The examination order is inputted from an external system, such as hospital information system (HIS) or radiation information system (RIS), which manages patient information and examination information relating to radiographic examination. Alternatively, the examination order is inputted manually by an operator such as a radiation technologist. Items regarding the body part to be imaged, such as head, chest, abdomen, hand, and finger are contained in the examination order. Additionally, the body part to be imaged includes an imaging direction such as front, side, oblique, PA (in which X-rays are irradiated from the rear of the object), and AP (in which X-rays are irradiated from the front of the object). The operator confirms the details of the examination order on the monitor 14b, and inputs the imaging condition corresponding to the details of the examination order through the operation screen displayed on the monitor 14b using the input device 14a.

The imaging condition includes, in addition to the body part to be imaged, tube voltage (unit; kV) for determining energy spectrum of the X-rays to be irradiated from the X-ray source 10, tube current (unit; mA) for determining a dose of the X-rays per unit of time, an irradiation time (unit;

s) of the X-rays, and the like, as shown in FIG. 6. The accumulated dose of the X-rays is defined by the product of the tube current and the irradiation time. As the imaging condition, instead of inputting the value of tube current and the value of irradiation time separately, the value of tube current-time product (mAs value) as the product of them is inputted in some cases.

Figure 2:
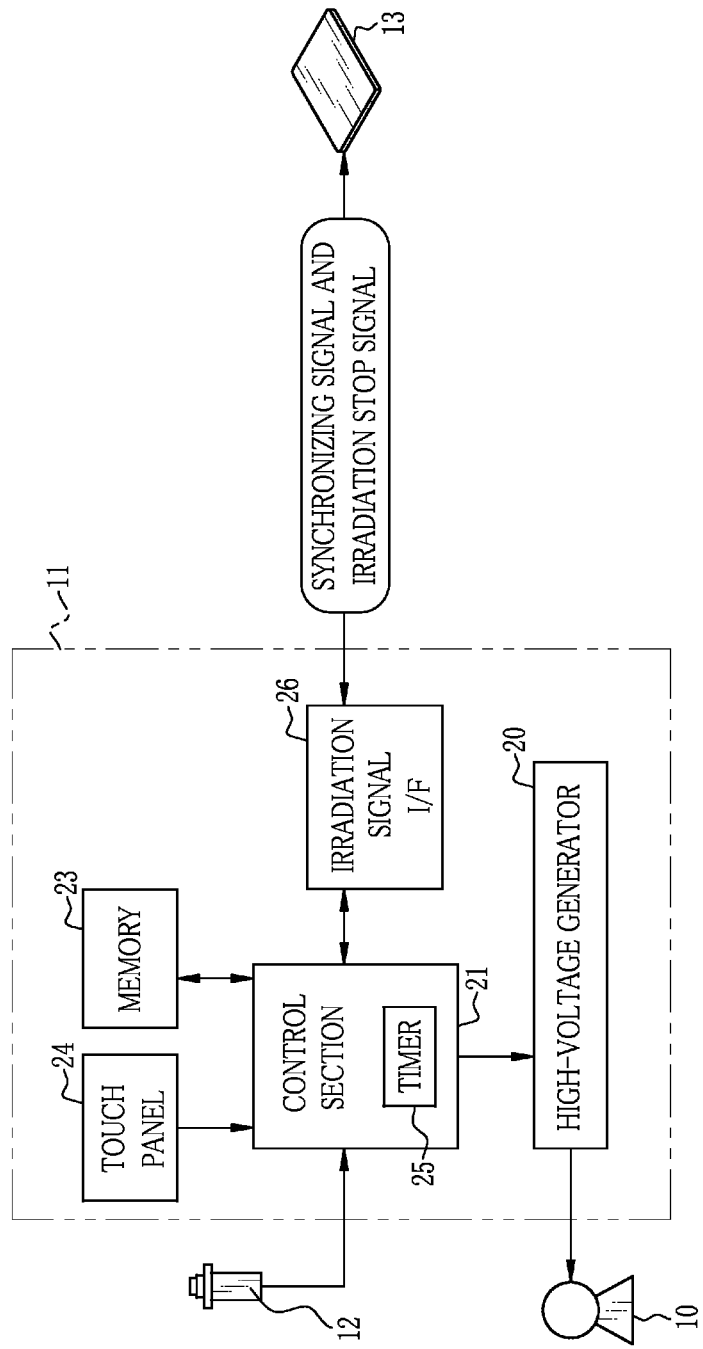
FIG. 2 is a view showing an internal structure of a source controller.

As shown in FIG. 2, the source controller 11 includes a high-voltage generator 20, a control section 21, a memory 23, a touch panel 24, and an irradiation signal I/F 26. The high-voltage generator 20 generates a high tube voltage by multiplying an input voltage using a transformer, and supplies the X-ray source 10 with the high tube voltage through a high-voltage cable. The control section 21 controls the tube voltage and the tube current to be supplied to the X-ray source 10, and the irradiation time of the X-rays. The irradiation signal I/F 26 mediates transmission and reception of signals to and from the electronic cassette 13.

The irradiation switch 12, the memory 23, and the touch panel 24 are connected to the control section 21. The irradiation switch 12 is a two-step push-button switch for inputting a command for actuating the control section 21. Upon first-step pressing (i.e. halfway pressing) of the irradiation switch 12, the control section 21 issues a warm-up start signal to the high-voltage generator 20 so as to start the warming-up of the X-ray source 10.

Upon first-step pressing (i.e. halfway pressing) of the irradiation switch 12 in a state that the electronic cassette 13 is connected to the irradiation signal I/F 26, the control section 21 transmits and receives a synchronizing signal to and from the electronic cassette 13 so as to achieve synchronization control. Upon second-step pressing (i.e. full pressing) of the irradiation switch 12, the control section 21 issues an irradiation start signal to the high-voltage generator 20 so as to start the X-ray irradiation from the X-ray source 10. In contrast, in a state that the electronic cassette 13 is not connected to the irradiation signal I/F 26, the transmission/reception of the synchronizing signal is not performed between the control section 21 and the electronic cassette 13, and the control section 21 promptly issues the irradiation start signal to the high-voltage generator 20 in response to the second-step pressing (i.e. full pressing) of the irradiation switch 12.

The memory 23 stores in advance several types of imaging conditions including the tube voltage, the tube current, the irradiation time, and the like. The imaging condition is set manually by the operator through the touch panel 24. A plurality types of imaging conditions read out from the memory 23 are displayed on the touch panel 24. The operator selects the same imaging condition as that inputted to the console 14 out of the imaging conditions displayed on the touch panel 24, so as to set the imaging condition for the source controller 11. As a matter of course, it is also possible to perform fine adjustment of the values included in the imaging condition preliminarily prepared. The control section 21 incorporates a timer 25 to be used for stopping the X-ray irradiation when the set irradiation time has elapsed. Note that, the imaging condition for the source controller 11 may be automatically set by transmitting the imaging condition, which is inputted to the console 14, to the source controller 11.

In order to prevent a shortage of the X-ray dose because of the reason that the X-ray irradiation is stopped before the accumulated dose reaches the target dose and a decision to stop the X-ray irradiation is made by the AEC function, the irradiation time with a margin is set, in the case where the AEC function of the electronic cassette 13 is used. The maximum value of the irradiation time, which is determined for each body part to be imaged in accordance with safety regulations in the X-ray source 10, also may be set. In the case where the AEC function is not used, the irradiation time is set in accordance with the body part to be imaged and the thickness of the object. The control section 21 controls the X-ray irradiation based on the tube voltage, the tube current, and the irradiation time set by the imaging condition. In the case where it is judged that the accumulated dose of the X-rays has reached the necessary and sufficient target dose, the X-ray irradiation is stopped by the AEC function even before the irradiation time preliminarily set in the source controller 11 is achieved.

The irradiation signal I/F 26 mediates transmission and reception of the synchronizing signals in the synchronization control performed between the source controller 11 and the electronic cassette 13. The control section 21 transmits an irradiation start request signal, which is a synchronizing signal for inquiring whether or not to permit the start of X-ray irradiation, to the electronic cassette 13 through the irradiation signal I/F 26, before the start of X-ray irradiation. In response to the irradiation start request signal, the control section 21 receives from the electronic cassette 13 an irradiation permission signal which is a synchronizing signal for indicating that the preparation for receiving the X-ray irradiation has been completed. Further, the irradiation signal I/F 26 receives an irradiation stop signal from the electronic cassette 13 when the electronic cassette 13 performs the AEC. The communication system of the irradiation signal I/F 26 may be in a wired manner or in a wireless manner.

Figure 3:
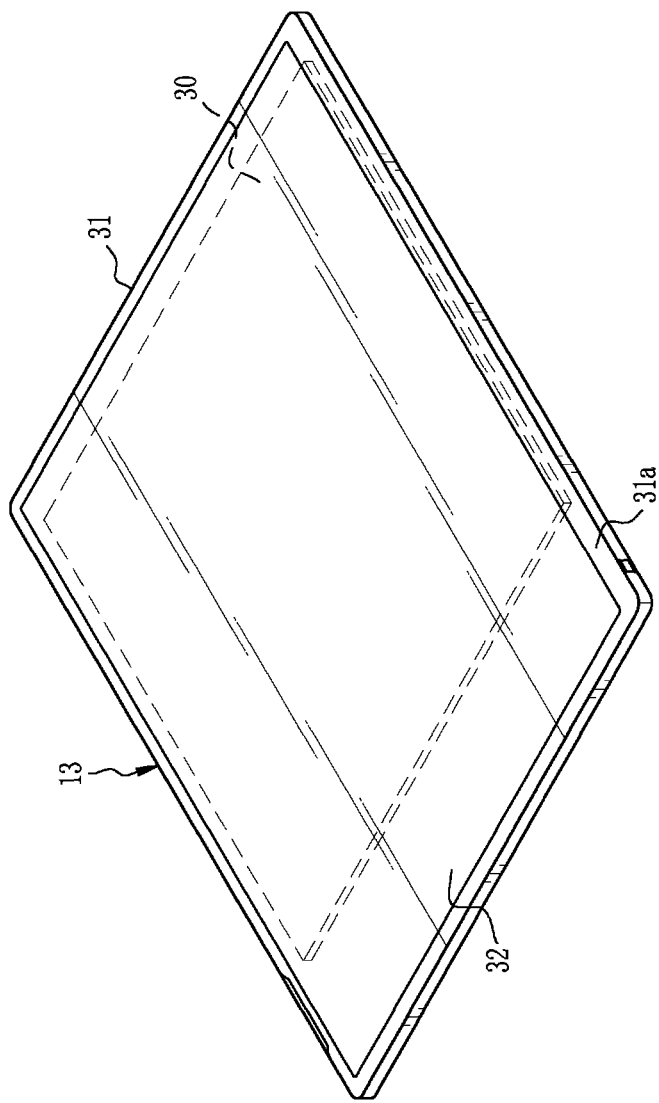
FIG. 3 is a perspective view showing an external appearance of an electronic cassette.

In FIG. 3, the electronic cassette 13 consists of a sensor panel 30 and a flat box-shaped portable housing 31 for containing the sensor panel 30. The housing 31 is formed from a conductive resin, for example. A front surface 31a of the housing 31, through which the X-rays enter, has an opening having a rectangular shape. A transparent plate 32 as a top panel is attached to the opening. The transparent plate 32 is formed from a carbon material that is lightweight and has high rigidity and high X-ray transparency. The housing 31 also functions as an electromagnetic shield for preventing electromagnetic noise from entering the electronic cassette 13 and for preventing electromagnetic noise from being emitted from the electronic cassette 13 to the outside. Note that, the housing 31 incorporates not only the sensor panel 30 but also a battery (secondary battery) for supplying electricity at a predetermined voltage to the respective components of the electronic cassette 13 and an antenna for use in wireless communication of data such as the X-ray images with the console 14.

The housing 31 has approximately the same size as those of a film cassette and an IP cassette, for example. The size of the housing 31 is compatible with International Standard ISO 4090:2001. Therefore, the electronic cassette 13 is detachably set to a holder 15a of the upright-posture imaging table 15 or a holder 16a of the supine-posture imaging table 16 (see FIG. 1), such that the front surface 31a of the housing 31 is held in a posture facing the X-ray source 10. Then, the X-ray source 10 is moved by the source moving device depending on the imaging table to be used. Further, in some cases, the electronic cassette 13 is put on a bed on which the object is lying, or held by the object itself, to be used solely, in stead of being set to the imaging table 15 or 16. Note that, since the electronic cassette 13 has approximately the same size as those of the film cassette and the IP cassette, the electronic cassette 13 can be set to an existing imaging table designed for the film cassette and the IP cassette.

Figure 4:
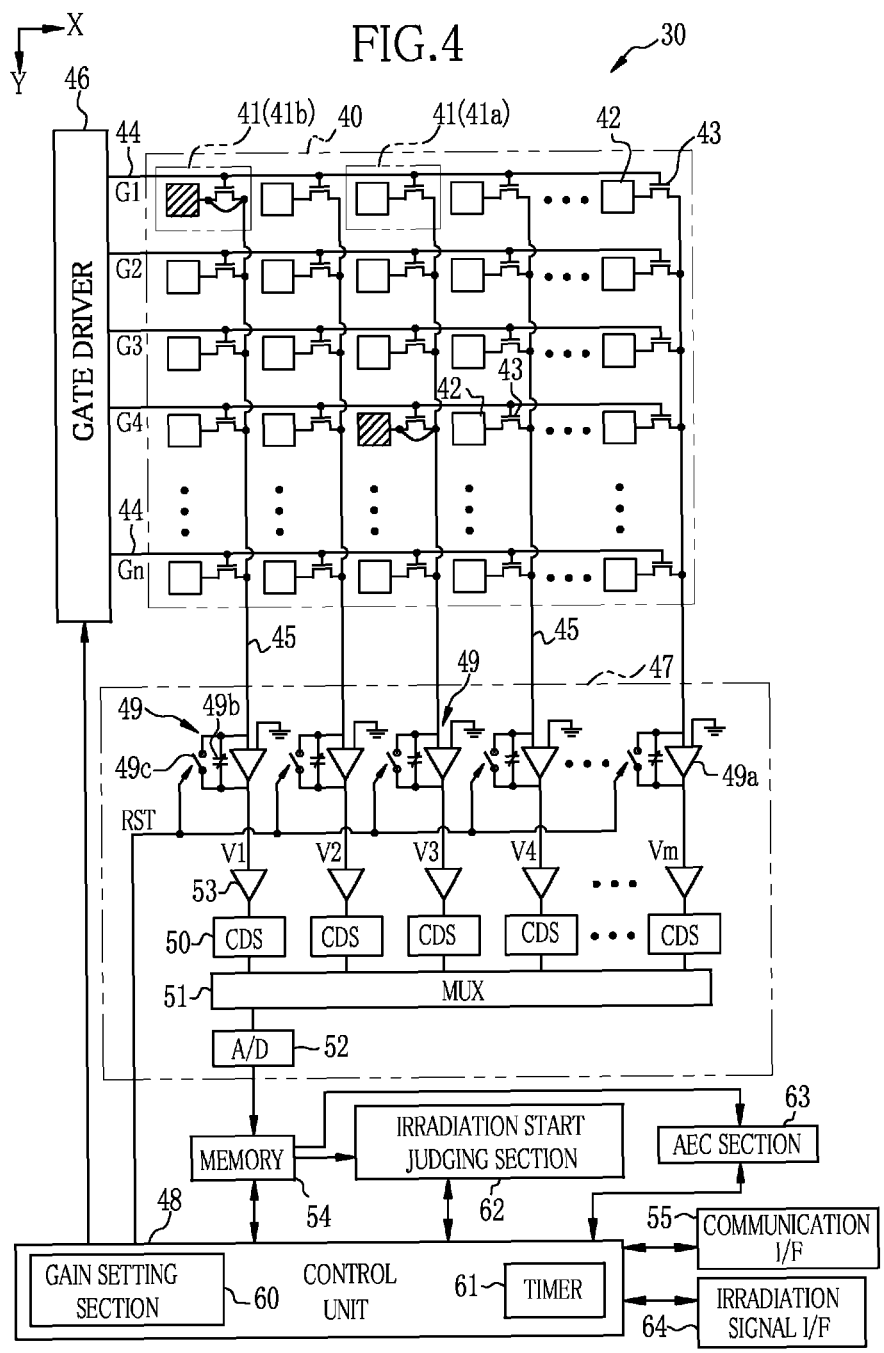
FIG. 4 is a block diagram showing an internal structure of the electronic cassette.

As shown in FIG. 4, the sensor panel 30 has a TFT active matrix substrate on which an imaging area 40 is formed. On the imaging area 40, a plurality of pixels 41 for accumulating electric charges corresponding to the received X-ray dose are arranged in a matrix form with n rows (that is along X direction) and m columns (that is along Y direction) at a predetermined pitch. Note that, each of n and m is an integer of two or more, and approximately equal to 2000 (i.e. n, m≈2000), for example. Note that, the pixels 41 may arranged in a honeycomb pattern instead of being arranged in a square pattern.

The sensor panel 30 has a scintillator (i.e. a phosphor, not shown in the drawing) for converting the X-rays into visible light. The sensor panel 30 is of an indirect-conversion type in which the visible light obtained by converting the X-rays by the scintillator is photoelectrically converted in the pixels 41. The scintillator is made of CsI:TI (thallium activated cesium iodide), GOS ($Gd_2O_2S$:Tb, terbium activated gadolinium oxysulfide), or the like, and is opposed to the entire surface of the imaging area 40 on which the pixels 41 are arranged. Note that, the scintillator and the TFT active matrix substrate may be disposed according to either a Penetration Side Sampling (PSS) system in which the scintillator and the substrate are disposed in this order from the X-ray incident side, or an irradiation side sampling (ISS) system in which the substrate and the scintillator are disposed in this order from the X-ray incident side, in contrast to the PSS system. Alternatively, a sensor panel of a direct-conversion type, which has a conversion layer (amorphous selenium or the like) for directly converting the X-rays into the electric charges without using the scintillator, may be used instead.

As well known, each of the pixels 41 includes a photoelectric converter 42 for generating the electric charges (electron-hole pairs) upon incidence of the visible light and accumulating the generated electric charges, and a TFT 43 as a switching element.

Each of the photoelectric converters 42 has a structure in which a semiconductor layer (for example, of a PIN (p-intrinsic-n) type) for generating electric charges is sandwiched between an upper electrode and a lower electrode. The TFT 43 is connected to the lower electrode of the photoelectric converter 42, and a bias line is connected to the upper electrode of the photoelectric converter 42. The number of the bias lines corresponds to the number of rows (n rows) of the pixels 41, and the bias lines are coupled to a single bus. The bus is connected to a bias power supply. A bias voltage is applied from the bias power supply to the upper electrode of each of the photoelectric converters 42 through the bus and the bias line as a subordinate of the bus. With the application of the bias voltage, an electric field is generated in the semiconductor layer, and the electric charges (electron-hole pairs) generated in the semiconductor layer by photoelectric conversion are moved to the upper electrode and the lower electrode, one of which has positive polarity, and the other of which has negative polarity. Thereby, the electric charges are accumulated in the photoelectric converters 42.

Each of the TFTs 43 has a gate electrode connected to a scanning line 44, a source electrode connected to a signal line 45, and a drain electrode connected to the photoelectric converter 42. The scanning lines 44 and the signal lines 45 are wired in a lattice shape. The number of the scanning lines 44 corresponds to the number of rows (n rows) of the pixels 41, such that one scanning line 44 is provided for the pixels 41 arranged in one row. Further, the number of the signal lines 45 corresponds to the number of columns (m columns) of the pixels 41, such that one signal line 45 is provided for the pixels 41 arranged in one column. The scanning lines 44 are connected to a gate driver 46, and the signal lines 45 are connected to a signal processing circuit 47.

Under the control of the control unit 48, the gate driver 46 drives the TFTs 43, such that the sensor panel 30 carries out an accumulation operation for accumulating the signal charges corresponding to the received X-ray dose in the pixels 41, a readout operation for reading out the signal charges accumulated in the pixels 41, and a reset operation. In the accumulation operation, the signal charges are accumulated in the pixels 41 while the TFTs 43 are turned off. In the readout operation, the gate driver 46 sequentially issues gate pulses G1 to Gn, each of which drives the TFTs 43 in the corresponding row at a time, at a predetermined time interval. Thereby, the scanning lines 44 are activated sequentially on a row-by-row basis, such that the TFTs 43 connected to the activated scanning lines 44 are turned on sequentially on a row-by-row basis. When the TFT 43 is turned on, the electric charges accumulated in the photoelectric converter 42 of each of the pixels 41 are read out to the signal line 45, and inputted to the signal processing circuit 47.

Dark charges are generated in the semiconductor layer of each of the photoelectric converters 42 irrespective of incidence of the X-rays. Due to the application of the bias voltage, the dark charges are accumulated in the photoelectric converter 42 of each of the pixels 41. The dark charges generated in the pixels 41 become noise components in the image data, and therefore the reset operation is carried out at a predetermined time interval so as to remove the dark charges before the X-ray irradiation is started. The reset operation is carried out to discharge the dark charges generated in the pixels 41 through the signal lines 45.

The reset operation is carried out by a sequential reset method, for example, by which the pixels 41 are reset on a row-by-row basis. In the sequential reset method, as with the readout operation of the signal charges, the gate driver 46 sequentially issues the gate pulses G1 to Gn to the scanning lines 44 at a predetermined time interval so as to turn on the TFTs 43 on a row-by-row basis.

Instead of the sequential reset method, a parallel reset method or an all-pixels reset method may be used. In the parallel reset method, a plurality of rows of pixels are grouped together, and the reset operation is sequentially carried out in each of the groups, so as to concurrently discharge the dark charges from the rows corresponding to the number of the groups. In the all-pixels reset method, the gate pulse is inputted to every row at the same time to discharge the dark charges from every pixel at a time. The parallel reset method and the all-pixels reset method enable the speeding up of the reset operation.

The signal processing circuit 47 includes integration amplifiers 49, correlated double sampling (CDS) circuits 50, a multiplexer (MUX) 51, an A/D converter (A/D) 52, and the like. The integration amplifier 49 is connected one-by-one to each of the signal lines 45. Each of the integration amplifiers 49 consists of an operational amplifier 49a and a capacitor 49b connected between input and output terminals of the operational amplifier 49a. The signal line 45 is connected to one of input terminals of the operational amplifier 49a. The other one of the input terminals of the operational amplifier 49a is connected to a ground (GND). To the capacitor 49b, a reset switch 49c is connected in parallel. Each of the integration amplifiers 49 integrates the electric charges inputted thereto through the signal line 45, converts the electric charges into analog voltage signals V1 to Vm, and outputs the analog voltage signals V1 to Vm.

A variable-capacity capacitor is used as the capacitor 49b of the integration amplifier 49. An output voltage signal V from each of the integration amplifiers 49 can be obtained by dividing "q" by "C" (namely, calculated by a mathematical expression denoted by V=q/c), in which "q" represents the accumulated charges and "C" represents a capacity of the capacitor 49b. Accordingly, since the variable-capacity capacitor is used as the capacitor 49 so as to change the capacity C of the capacitor 49b, it is possible to change the gain to be applied to the voltage signal by the integration amplifier 49. The gain of the integration amplifier 49 is set by a gain setting section 60 in the control unit 48.

An output terminal of the operational amplifier 49a in each column is connected to the MUX 51 through an amplifier 53 and the CDS circuit 50. The A/D 52 is connected to the output side of the MUX 51. The CDS circuit 50, each having a sample-and-hold circuit, applies correlated double sampling to the output voltage signal from the integration amplifier 49, so as to remove kTC noise components from the integration amplifier 49 and hold the output voltage signal from the integration amplifier 49 for a predetermined period of time in the sample-and-hold circuit (i.e. performs sample holding). The MUX 51 sequentially selects one of the CDS circuits 50 connected in parallel from every row with use of an electronic switch based on an operation control signal from a shift resister (not shown in the drawing), such that the voltage signals V1 to Vm outputted from the selected CDS circuits 50 are serially inputted to the A/D 52. Further, another amplifier may be connected between the MUX 51 and the A/D 52.

The A/D 52 converts the inputted analog voltage signals V1 to Vm corresponding to one row into a digital value, and outputs the digital value to a memory 54 contained in the electronic cassette 13. The memory 54 stores the digital value corresponding to one row in association with coordinates of each of the pixels 41 as image data of the X-ray image corresponding to one row. Thereby, the readout operation corresponding to one row is completed.

After the MUX 51 reads out the voltage signals V1 to Vm corresponding to one row from the integration amplifiers 49, the control unit 48 outputs a reset pulse RST to the integration amplifiers 49, such that the reset switches 49c are turned on. Thereby, the signal charges corresponding to one row accumulated in the capacitors 49b are discharged, and the integration amplifiers 49 are reset. After the integration amplifiers 49 are reset, the reset switches 49c are turned off again. After a lapse of a predetermined period of time from the turning off of the reset switches 49c, one of the sample-and-hold circuits of each of the CDS circuits 50 is held so as to sample the kTC noise components of the integration amplifier 49. Thereafter, the gate pulse corresponding to the next row is outputted from the gate driver 46 so as to start reading out the signal charges from the pixels 41 of the next row. After a lapse of a predetermined period of time from the outputting of the gate pulse, the signal charges of the pixels 41 of the next row are held by another one of the sample-and-hold circuits of each of the CDS circuits 50. By repetition of the above operation, the signal charges are read out from the pixels 41 of every row.

After the completion of the readout operation from every row, the image data representing one sheet of the X-ray image is stored in the memory 54. The image data is read out from the memory 54, subjected to various types of image processing in the control unit 48, and then outputted to the console 14 through a communication I/F 55. Thereby, the X-ray image of the object is detected.

The communication I/F 55 is connected to the console 14 in a wired or wireless manner to mediate transmission and reception of information to and from the console 14. The communication I/F 55 receives the imaging condition inputted by the operator from the console 14, and inputs the information of the imaging condition to the control unit 48.

Note that, in the reset operation, while the TFTs 43 are turned on, dark charges from the pixels 41 flow into the capacitors 49b of the integration amplifiers 49 through the signal lines 45. Unlike the readout operation, the MUX 51 does not read out the electric charges accumulated in the capacitors 49b, and in synchronization with the issue of each of the gate pulses G1 to Gn, the control unit 48 outputs the reset pulse RST. Thereby, the reset switches 49c are turned on, and the electric charges accumulated in the capacitors 49b are discharged, such that the integration amplifiers 49 are reset.

The control unit 48 includes a gain setting section 60. The gain setting section 60 changes the capacity of the capacitor 49b of the integration amplifier 49 so as to set the gain of the integration amplifier 49. An internal memory in the control unit 48 stores a value of the gain of the integration amplifier 49 in each of the case where it is determined that the irradiation start judging function is used by the console 14 and the case where it is determined that the AEC function is used by the console 14. The gain setting section 60 selectively reads out the value of the gain from the internal memory depending on the setting information from the console 14, and sets the value of the gain read out from the internal memory to the integration amplifier 49. The gain setting section 60 sets the gain of the integration amplifier 49 in the case where it is determined that the irradiation start judging function is used by the console 14 lower than that in the case where it is determined that the AEC function is used by the console 14. For example, the gain of the integration amplifier 49 in the case where it is determined that the irradiation start judging function is used is set to be 1/10 of that in the case where it is determined that the AEC function is used.

Additionally, the control unit 48 incorporates a timer 61. The timer 61 operates in the case where the irradiation start judging function is used. In the case where the AEC function is used, the accumulated dose is compared with the target dose, so as to decide whether or not to stop the X-ray irradiation. However, in the case where the irradiation start judging function is used, the AEC function does not operate. Therefore, instead, the timer 61 is used to measure the X-ray irradiation time. The irradiation time set as an item of the imaging condition by the console 14 is set to the timer 61. The timer 61 starts measuring the X-ray irradiation time when the irradiation start judging section 62 judges that the X-ray irradiation has been started. The control unit 48 determines that the X-ray irradiation has been stopped when the X-ray irradiation time measured by the timer 61 achieves the X-ray irradiation time set as the item of the imaging condition by the console 14.

The control unit 48 includes not only the gain setting section 60 and the timer 61 but also circuits for subjecting the X-ray image data in the memory 54 to various types of image processing such as offset correction, sensitivity correction, and defect correction (not showing in the drawings). The offset correction circuit subtracts an offset correction image, which is obtained from the sensor panel 30 without irradiation of the X-rays, from the X-ray image on a pixelby-pixel basis, in order to remove fixed pattern noise caused by the individual difference of the signal processing circuit 47 and imaging environment. The sensitivity correction circuit, which is also called as a gain correction circuit, corrects variations in the sensitivity of the photoelectric converter 42 of each of the pixels 41, variations in the output property of the signal processing circuit 47, and the like. The defect correction circuit performs linear interpolation of a pixel value of a defect pixel using a pixel value of a normal pixel around the defect pixel, based on defect pixel information produced at the time of shipping or periodic inspection. Further, the defect correction circuit corrects the pixel value of each of the pixels 41 in a column in which the detection pixel 41b is disposed in the similar manner as described above. Note that, the circuits for subjecting the X-ray image data in the memory 54 to various types of image processing may be disposed in the console 14 so as to perform the various types of image processing in the console 14.

As the pixels 41, there are normal pixels 41a and the detection pixels 41b. The normal pixels 41a are used to produce the X-ray image. The detection pixels 41b, on the other hand, function as dose detection sensors for detecting the X-ray dose received by the imaging area 40. The detection pixels 41b are used for the judgment on whether or not the X-ray irradiation has been started or the AEC. The positions of the detection pixels 41b are already known at the time of manufacturing the sensor panel 30, and the sensor panel 30 has a nonvolatile memory (not shown in the drawing) for storing the position (coordinates) of every detection pixel 41b in advance. Note that, in the drawing, the detection pixels 41b are hatched so as to be distinguished from the normal pixels 41a.

The basic structure including the photoelectric converter 42 and the like is exactly the same between the normal pixel 41a and the detection pixel 41b. Thus, the normal pixel 41a and the detection pixel 41b can be formed by almost the same manufacturing process. The TFT 43 of each of the detection pixels 41b has a short between the source electrode and the drain electrode. Therefore, the electric charges generated in the photoelectric converter 42 of each of the detection pixels 41b flow into the signal line 45 irrespective of whether the TFT 43 is turned on or turned off, and the TFTs 43 of the normal pixels 41a in the same row are turned off. Thereby, it is possible to read out the electric charges even while the accumulation operation for accumulating the signal charges is performed.

The electric charges generated in the photoelectric converter 42 of each of the detection pixels 41b flow into the capacitor 49b of the integration amplifier 49 through the signal line 45. The electric charges of the detection pixels 41b accumulated in the integration amplifiers 49 are outputted to the A/D 52, and converted into a digital voltage signal (hereinafter referred to as a dose signal) by the A/D 52. The dose signal is outputted to the memory 54 and stored in the memory 54 in association with the information of coordinates of the detection pixels 41b in the imaging area 40. The sensor panel 30 repeats such a dose detection operation several times at a predetermined sampling period $\Delta t$ (see FIGS. 8 and 9) which is the same as that at the time of performing the readout operation. The memory 54 stores the dose signals from all the detection pixels 41b per one sampling. Note that, the sampling period $\Delta t$ of the dose signal in this embodiment is a period from when the capacitor 49b of the integration amplifier 49 starts integrating the electric charges generated in the photoelectric converter 42 of each of the detection pixels 41b to when the voltage signal obtained by converting the integrated electric charges is outputted to the CDS circuit 50 (namely, integration period of the integration amplifier 49).

In the case where it is determined that the irradiation start judging section 62 is used, the sensor panel 30 starts the dose detection operation when the imaging condition set by the console 14 is inputted through the communication I/F 55 to the control unit 48. On the other hand, when it is determined that the AEC section 63 is used, in response to the irradiation start request signal from the source controller 11, the dose detection operation is started when the irradiation permission signal is transmitted from the irradiation signal I/F 64.

The control unit 48 determines which of the irradiation start judging section 62 and the AEC section 63 is used based on the setting information from the console 14. The irradiation start judging section 62 and the AEC section 63 are set to be used alternatively, for example.

Operation of each of the irradiation start judging section 62 and the AEC section 63 is controlled by the control unit 48. Each of the irradiation start judging section 62 and the AEC section 63 reads out the dose signal obtained at the predetermined sampling period $\Delta t$ from the memory 54 each time the sampling is performed, such that the judgment on whether or not the X-ray irradiation has been started and the AEC are performed based on the dose signal read out from the memory 54.

The irradiation start judging section 62 compares the maximum value of the dose signal of each of the detection pixels 41b, which is read out from the memory 54, with a preliminarily-set irradiation start threshold value each time the sampling is performed. In the case where the maximum value of the dose signal exceeds the irradiation start threshold value, the irradiation start judging section 62 judges that the X-ray irradiation from the X-ray source 10 has been started (namely, the X-rays from the X-ray source 10 has reached the imaging area 40), and outputs a signal indicating that the irradiation start judging section 62 judges that the X-ray irradiation has been started (hereinafter referred to as irradiation start judgment signal) to the control unit 48. The irradiation start threshold value is set to be same irrespective of the imaging condition.

The AEC section 63 sequentially adds up the dose signals, which are read out from the memory 54 at the sampling performed several times, for each of the coordinates so as to measure the accumulated dose of X-rays reaching the imaging area 40. More specifically, the AEC section 63 calculates a representative value (an average value, a maximum value, a mode value, or a total value is also available) of the dose signals from the detection pixels 41b in the dose measurement field based on the information of the dose measurement field provided by the console 14, and integrates the representative values, so as to obtain the accumulated dose in the dose measurement field.

As a method for determining the dose measurement field, the following may be performed. In each of the plurality of blocks obtained by dividing the imaging area 40, the representative value of the dose signal is integrated, and the block having the minimum integrated value may be set as the dose measurement field. Alternatively, an arbitrary portion in the imaging area 40 may be designated as the dose measurement field in accordance with the setting by the operator.

The AEC section 63 compares the obtained accumulated dose in the dose measurement field with a preliminarily-set irradiation stop threshold value (i.e. target dose) each time the sampling is performed, and judges whether or not the accumulated dose has reached the irradiation stop threshold value. When the AEC section 63 judges that the accumulated dose in the dose measurement field exceeds the irradiation stop threshold value and the accumulated dose of the X-rays has reached the target dose, the AEC section 63 outputs the irradiation stop signal to the control unit 48.

The irradiation signal I/F 26 of the source controller 11 is connected to an irradiation signal I/F 64 in a wired or wireless manner. The irradiation signal I/F 64 mediates transmission and reception of the synchronizing signal to and from the source controller 11 in the synchronization control. Specifically, the irradiation signal I/F 64 mediates reception of the irradiation start request signal from the source controller 11 and transmission of the irradiation permission signal in response to the irradiation start request signal to the source controller 11. Additionally, the irradiation signal I/F 64 receives the irradiation stop signal outputted from the AEC section 63 through the control unit 48, and transmits the irradiation stop signal to the source controller 11.

Figure 5:
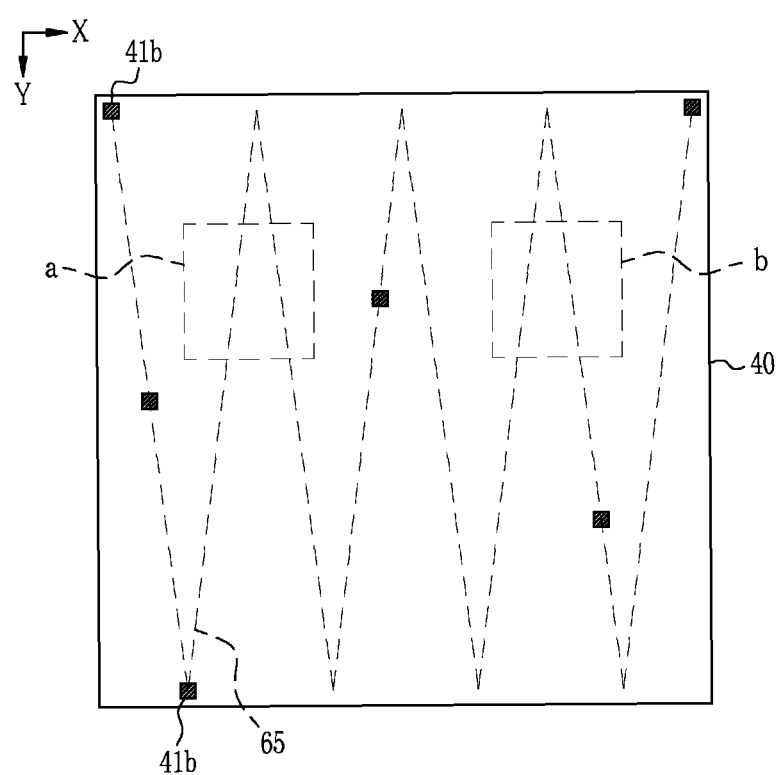
FIG. 5 is a view showing arrangement of detection pixels.

The detection pixels 41*b* are disposed along a waveform line 65 that is horizontally symmetric with respect to the center of the imaging area 40 as shown by a dashed line in FIG. 5. The detection pixel 41*b* is laid out one by one in the column of the pixels 41 connected to the single signal line 45. The column having the detection pixel 41*b* is arranged at intervals of two to three columns having no detection pixel 41*b*, for example.

The storage device 14*c* of the console 14 stores an imaging condition table 70 in which a plurality of imaging conditions are recorded in advance as shown in FIG. 6. The imaging condition includes the body part to be imaged, the tube voltage, the tube current, the irradiation time, the dose measurement field, and the irradiation stop threshold value. The dose measurement field represents a field in which the accumulated dose is calculated by the AEC section 63, and corresponds to a region of interest which is the most remarkable in diagnosis. Additionally, a portion at which a dose signal can be stably obtained is set for each body part to be imaged. For example, in the case where the body part to be imaged is a chest portion, left and right lung fields as shown by portions assigned with the reference symbols "a" and "b" in FIG. 5 are set as the dose measurement field. The dose measurement field is represented by X and Y coordinates. In the case where the dose measurement field is rectangular, for example, the X and Y coordinates of two points connected by a diagonal line are stored. The X and Y coordinates correspond to the positions of the pixels 41 including the detection pixels 41*b* in the imaging area 40. The coordinates of the upper left pixel 41 are assigned as an origin point (0, 0). The irradiation stop threshold value is information which is compared with the accumulated dose in the dose measurement field and enables the AEC section 63 to judge whether or not the X-ray irradiation has been stopped as described above.

The console 14 reads out the imaging condition corresponding to the command inputted by the operator from the imaging condition table 70. Further, the console 14 receives the setting for which of the irradiation start judging section 62 and the AEC section 63 is used. The console 14 transmits the imaging condition read out from the imaging condition table 70 and the received setting information to the electronic cassette 13.

As a method of setting for which of the irradiation start judging section 62 and the AEC section 63 is used, instead of or in addition to using the console 14 as described above, a selection switch may be provided to the housing 31 of the electronic cassette 13 such that the operator can select the irradiation start judging section 62 or the AEC section 63. Thereby, the selected irradiation start judging section 62 or AEC section 63 is operated in accordance with the manipulation of the selection switch. Alternatively, the irradiation signal I/F 64 may be provided with the function of detecting whether or not the irradiation signal I/F 26 of the source controller 11 is connected thereto such that an intercommunication channel such as the synchronizing signal is established between the irradiation signal I/F 26 and irradiation signal I/F 64. In the case where the irradiation signal I/F 64 detects that the intercommunication channel is not established, the irradiation start judging section 62 may be operated. On the other hand, in the case where the irradiation signal I/F 64 detects that the intercommunication channel is established, the AEC section 63 may be operated.

The electronic cassette 13 receives the imaging condition and the setting information through the communication I/F 55, and inputs the received imaging condition and the setting information to the control unit 48. In the case where the irradiation start judging section 62 is set to be used, the control unit 48 provides the timer 61 with the information of the irradiation time contained in the imaging condition. In contrast, in the case where the AEC section 63 is set to be used, the control unit 48 provides the AEC section 63 with the information of the dose measurement field and the irradiation stop threshold value contained in the imaging condition.

Figure 7:
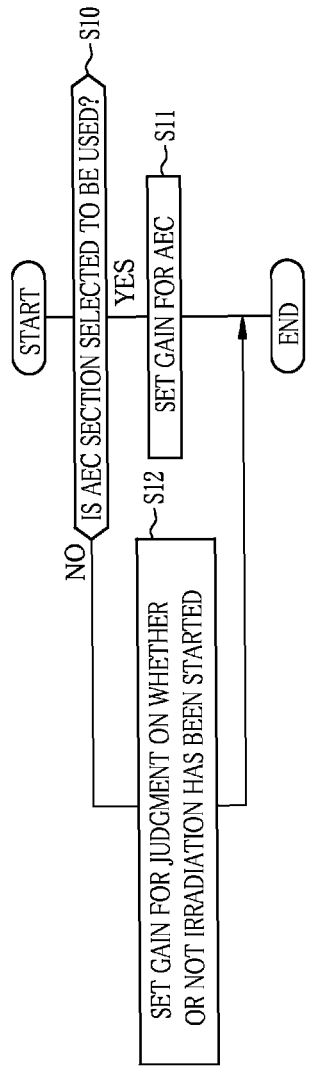
FIG. 7 is a flowchart showing a procedure for setting a gain of an integration amplifier.
Figure 8:
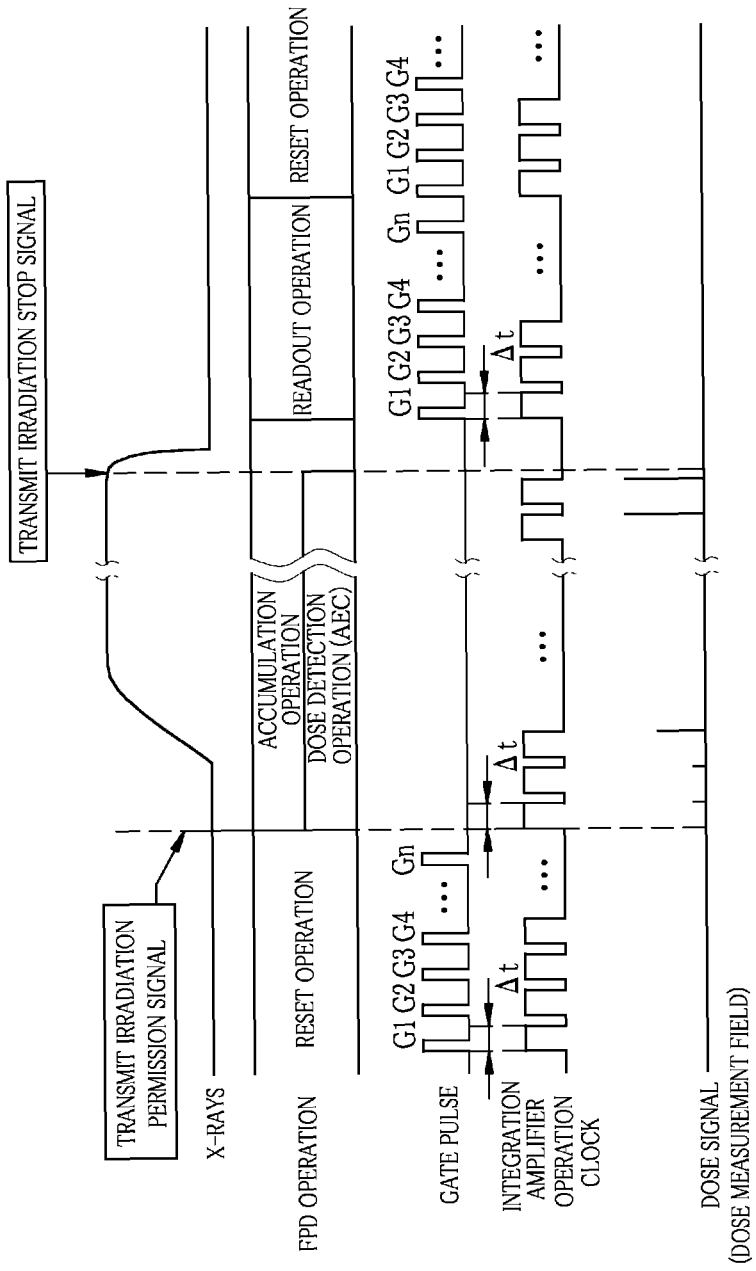
FIG. 8 is a view showing a shift in operation of a sensor panel in the case where an AEC section is used.

Next, with reference to FIGS. 7 to 9, the procedure for performing X-ray imaging once by the X-ray imaging system 2 is explained. At first, the case in which the irradiation signal I/F 26 of the source controller 11 is connected to the irradiation signal I/F 64 of the electronic cassette 13 in a wired or wireless manner, the intercommunication channel such as the synchronizing signal is established between the source controller 11 and the electronic cassette 13, and the AEC section 63 performs the AEC is explained hereinbelow.

At first, the object is set to a predetermined imaging position on one of the upright-posture imaging table 15 and the supine-posture imaging table 16. Positioning is performed by adjusting a height and a horizontal position of the electronic cassette 13 to the body part of the object to be imaged. Then, a height and a horizontal position of the X-ray source 10, and a size of the irradiation field of the X-rays from the X-ray source 10 are adjusted in accordance with the position of the electronic cassette 13 and the size of the body part to be imaged. Next, the imaging condition is set in the source controller 11 and the console 14. Additionally, the AEC 63 is set to be used in the console 14 (YES in step S10 in FIG. 7). Thus, the gain setting section 60 reads out the value of gain for AEC from the internal memory of the control unit 48, and sets the value of gain for AEC in the integration amplifier 49 (step S11 in FIG. 7).

Upon completion of the preparation for X-ray imaging, the operator presses the irradiation switch 12 halfway. Upon the halfway pressing of the irradiation switch 12, the source controller 11 issues the warm-up start signal to the high-voltage generator 20 so as to start the warming-up of the X-ray source 10. Further, the source controller 11 transmits the irradiation start request signal to the electronic cassette 13.

In FIG. 8, before the X-ray imaging, the sensor panel 30 of the electronic cassette 13 repeats the reset operation and waits for the irradiation start request signal. Upon receiving the irradiation start request signal from the source controller 11, the sensor panel 30 checks a state of the electronic cassette 13, and then transmits the irradiation permission signal to the source controller 11. Concurrently, the sensor panel 30 finishes the reset operation and starts the accumulation operation and the dose detection operation.

Upon reception of the irradiation permission signal from the sensor panel 30 and full pressing of the irradiation switch 12, the source controller 11 issues the irradiation start signal to the high-voltage generator 20 so as to start X-ray irradiation from the X-ray source 10. The X-rays irradiated from the X-ray source 10 pass through the object and enter the sensor panel 30.

In the sensor panel 30, the electric charges generated in the normal pixels 41*a* are accumulated in the photoelectric converters 42. However, since the TFTs are short-circuited, the electric charges generated in the detection pixels 41*b* flow into the capacitors 49*b* of the integration amplifiers 49 through the signal lines 45. In the sensor panel 30, the electric charges generated in the detection pixels 41*b* are repeatedly read out with the gain for AEC set by the gain setting section 60 at the predetermined sampling period Δt. The dose signal obtained by the sampling is stored in the memory 54, and read out from the memory 54 to the AEC section 63 each time the sampling is performed.

The AEC section 63 calculates the accumulated dose in the dose measurement field based on the dose signal readout from the memory 54 and the information of the dose measurement field provided by the console 14. Then, the AEC section 63 compares the accumulated dose in the dose measurement field and the irradiation stop threshold value, so as to judge whether or not the accumulated dose has reached the irradiation stop threshold value.

When the accumulated dose in the dose measurement field exceeds the irradiation stop threshold value and the AEC section 63 judges that the accumulated dose has reached the target dose, the AEC section 63 issues the irradiation stop signal. The irradiation stop signal is transmitted to the source controller 11. Upon receiving the irradiation stop signal, the source controller 11 stops the X-ray irradiation from the X-ray source 10.

After the transmission of the irradiation permission signal, the accumulation operation is performed in the normal pixels 41*a* in the sensor panel 30. After the AEC section 63 judges that the accumulated dose in the dose measurement field has reached the target dose and a predetermined period of time has elapsed after the output of the irradiation stop signal, the operation of the sensor panel 30 shifts from the accumulation operation to the readout operation. Thereby, the image data representing one sheet of X-ray image is outputted to the memory 54. After the readout operation, the operation of the panel 30 returns to the reset operation.

Note that, in an irradiation profile of X-rays, the dose does not become zero immediately after the irradiation stop signal is outputted, and a wave tail is generated. In order to absorb the wave tail, after a predetermined period of time elapses from the transmission of the irradiation stop signal, the operation of the panel 30 is shifted from the accumulation operation to the readout operation is performed in this embodiment.

The X-ray image outputted to the memory 54 in the readout operation is subjected to the various types of image processing by the various image processing circuits in the control unit 48. The X-ray image subjected to the image processing is transmitted to the console 14, and displayed on the monitor 14*b* to be used for diagnosis. Thereby, the procedure for performing X-ray imaging once is completed.

Next, the case in which the irradiation start judging section 62 is set to be used in the console 14 (NO in step S10 in FIG. 7) and the irradiation start judging section 62 judges whether or not the X-ray irradiation has been started is explained hereinbelow. In this case, the gain setting section 60 reads out the value of gain for the judgment on whether or not the X-ray irradiation has been started, which is lower than that for the AEC, from the internal memory of the control unit 48, and sets the read-out value of gain in the integration amplifier 49 (step S12 in FIG. 7). Note that, the judgment on whether or not the X-ray irradiation has been started is performed in the case where the source controller 11 and the electronic cassette 13 cannot be connected to each other due to the layout or in the case where the signal cable to be connected to the source controller 11 hinders the handling of the electronic cassette 13 to be used solely and therefore the source controller 11 and the electronic cassette 13 cannot be connected to each other.

In this case, as shown in FIG. 9, upon receiving the imaging condition from the console 14, the sensor panel 30 finishes the reset operation and starts the dose detection operation. Concurrently, since the TFTs 43 are turned off, the electric charges are also accumulated in the normal pixels 41*a*. However, the electric charges are discharged in the reset operation after the judgment on whether or not the X-ray irradiation has been started.

Further, in this case, the source controller 11 does not transmit/receive the synchronizing signals. Upon full pressing of the irradiation switch 12, the source controller 11 issues the irradiation start signal to the high-voltage generator 20, so as to start the X-ray irradiation from the X-ray source 10.

The sensor panel 30 repeatedly reads out the electric charges generated in the detection pixels 41*b* with the gain set by the gain setting section 60 at the predetermined sampling period Δt. The dose signal obtained by the sampling is stored in the memory 54, and read out from the memory 54 to the irradiation start judging section 62 each time the sampling is performed.

There is a time lag from when the preparation for the X-ray imaging is ready to when the X-rays are actually irradiated from the X-ray source 10. During the period of time from when the preparation for the X-ray imaging is ready to when the X-rays are actually irradiated from the X-ray source 10, the dose signal has an extremely low value based on the dark charges generated in the detection pixels 41*b*. Actually, when the X-rays irradiated from the X-ray source 10 reach the sensor panel 30, the amount of electric charges generated in the detection pixels 41*b* is increased due to the sympathetic reaction of the detection pixels 41*b*, and thereby the signal value of the dose signal is increased.

The irradiation start judging section 62 compares the maximum value of the dose signal of each of the detection pixels 41*b* which is read out from the memory 54 with the irradiation start threshold value each time the sampling is performed, so as to judge whether or not the X-ray irradiation has been started. In the case where the maximum value of the dose signal exceeds the irradiation start threshold value, the irradiation start judging section 62 issues the irradiation start judgment signal to the control unit 48.

Upon receiving the irradiation start judgment signal, the control unit 48 makes the sensor panel 30 perform the reset operation once and start the accumulation operation. Thereby, the timing for starting the X-ray irradiation is synchronized with the timing for starting the accumulation operation by the sensor panel 30. Concurrently, the timer 61 of the control unit 48 starts measuring the irradiation time.

When the irradiation time measured by the timer 61 has reached the irradiation time provided by the console 14, the control unit 48 shifts the operation of the sensor panel 30 from the accumulation operation to the readout operation. Further, when the irradiation time measured by the timer 25 has reached the set irradiation time, the source controller 11 stops the X-ray irradiation from the X-ray irradiation source 10. The subsequent processing is the same as that shown in FIG. 8, and therefore the explanation thereof will be omitted.

In the case where the AEC section 63 is used, the gain setting section 60 sets a relatively high gain to the integration amplifier 49. If the gain set to the integration amplifier 49 in the case of using the irradiation start judging section 62 is equal to or higher than that in the case of using the AEC section 63, not only the dose signal but also the random noise is extremely increased in a state that random noise is added to the dose signal, and the dose signal exceeds the irradiation start threshold value. As a result, the probability of misjudgment that the X-ray irradiation has been started is increased despite the fact that the X-rays have not been irradiated actually. Therefore, the gain at the time of using the irradiation start judging section 62 is set to be lower than that at the time of using the AEC section 63.

In the AEC, the dose signal having a relatively low value based on the X-rays having passed through the object is necessarily treated. In particular, in the case where the object is thick, the value of the dose signal from the detection pixels 41b contained in the dose measurement field is extremely low. Accordingly, in the case where the AEC section 63 is used, the gain to be set to the integration amplifier 49 is high such that the dose signal has a value at a level to be treated by the AEC section 63.

In the AEC, the integrated value of the dose signals is monitored during the X-ray irradiation, so as to perform the control for stopping the X-ray irradiation. Therefore, the dose signals obtained by the sampling performed several times are integrated and the integrated value thereof is compared with the irradiation stop threshold value. The random noise added to the dose signals obtained by the sampling performed several times includes random noise as positive components for increasing the signal value of the dose signal and random noise as negative components for decreasing the signal value of the dose signal in a mixed state. Therefore, the increase/decrease in the signal components due to the random noise is canceled in the course of integrating the dose signal obtained by each sampling, and as a result, the random noise becomes less prominent. Consequently, in the AEC, even if the gain of the integration amplifier 49 is set to be high, the signal components of the integrated value are increased, and therefore it is possible to secure a high S/N ratio.

In contrast, since it is judged whether or not the X-ray irradiation has been started by using the dose signal obtained at the instant corresponding to the rising period of the X-ray irradiation profile, the degree of cancellation between positive components and negative components in the random noise is small. In the case where the judgment on whether or not the X-ray irradiation has been started is performed based on the dose signal obtained by each sampling as with the case of this embodiment, the positive and negative components in the random noise are not cancelled, and directly affect the S/N ratio of the dose signal. Even if the dose signals obtained by the sampling performed several times are integrated and the judgment on whether or not the X-ray irradiation has been started is performed based on the integrated value as in the case of performing the AEC, due to the fact that the sampling period is short, the degree of cancellation between positive and negative components in the random noise is smaller than that in the case of performing the AEC. Accordingly, in the case where the gain of the integration amplifier 49 in the case of performing the judgment on whether or not the X-ray irradiation has been started is set to be equal to or higher than that in the case of performing the AEC, the amplification of the positive or negative components in the random noise seriously affects the judgment result. According to the present invention, since the gain to be set to the integration amplifier 49 at the time of using the irradiation start judging section 62 is lower than that at the time of using the AEC section 63, the probability of misjudgment on whether or not the X-ray irradiation has been started due to the random noise can be decreased.

Although one of the judgment on whether or not the X-ray irradiation has been started and the AEC is performed in the first embodiment, both of them may be performed in X-ray imaging once. Further, although the gain of the integration amplifier 49 is changed in the first embodiment, a gain-variable amplifier may be used as the amplifier 53 so as to change the gain of the amplifier 53.

Second Embodiment

According to the first embodiment, in both of the case where the irradiation start judging section 62 is used and the case where the AEC section 63 is used, the sampling period of the dose signal is set to Δt, which is the same as that at the time of performing the readout operation. However, the sampling period at the time of using the irradiation start judging section 62 may be different from the sampling period at the time of using the AEC section 63.

Specifically, as shown in FIG. 10, the sampling period of the dose signal in the case of using the irradiation start judging section 62 is set to Δt' which is shorter than Δt used in the first embodiment. The length of Δt' is half of the length of Δt, for example. The control unit 48 controls operation of the respective components of the signal processing circuit 47 such that the sampling period is set to Δt' in the case of using the irradiation start judging section 62 and the sampling period is set to Δt in the case of using the AEC section 63. Since the sampling period of the dose signal at the time of judging whether or not the irradiation has been started is made shorter, it is possible to perform judgment on whether or not the irradiation has been started more promptly.

Note that, the sampling period in the AEC may be made longer. For example, the sampling period in the AEC may be twice as long as Δt. The dose signal treated in the AEC often has a relatively low value based on the X-rays having passed through the object. Therefore, if the sampling period is made longer, it is possible to increase the value of the dose signal obtained by the sampling performed once.

Further, irrespective of the judgment on whether or not the irradiation has been started and the AEC, in the case where a relatively low tube current is set or in the case where the body part of the object to be imaged is relatively thick, namely, in the case where it is estimated that the value of the dose signal becomes lower than a standard value, fine adjustment may be made on the sampling period of the dose signal in accordance with the tube current or the thickness of the object (i.e. the body part to be imaged), by making the sampling period of the dose signal slightly longer, for example. As shown by a portion surrounded by a dashed line in FIG. 10, for example, in the case where the sampling period is set to Δt' at the time of using the irradiation start judging section 62, if the tube current is lower than the standard value or the object is thick, the sampling period is set to Δt'α. In contrast, in the case where the tube current is high than the standard value or the object is thin, the sampling period is set to $\Delta t'-\alpha$. Similarly, fine adjustment may be also made on the gain of the integration amplifier 49 in accordance with the tube current or thickness of the object. For example, in the case where the tube current is lower than the standard value or in the case where the object is thick, the gain is slightly increased, and in contrast, in the case where the tube current is higher than the standard value or in the case where the object is thin, the gain is slightly decreased.

Third Embodiment

Although the TFT 43 of each of the detection pixels 41 has a short between the source electrode and the drain electrode in the first embodiment, the detection pixel may be a pixel in which the TFT 43 is not provided and the photoelectric converter 42 is directly connected to the signal line 45. Alternatively, a detection pixel 41*c* shown in FIG. 11 may be adopted. Note that, the same components as those in the first embodiment are denoted by the same reference numerals, and the explanation thereof will be omitted.

In FIG. 11, the sensor panel 90 has the detection pixels 41*c*, each of which is connected to a TFT 93 driven by a scanning line 91 and a gate driver 92, while the scanning line 91 and the gate driver 92 are respectively different from the scanning line 44 and the gate driver 46 for driving the TFT 43 of the normal pixel 41*a*. Since each of the detection pixels 41*c* is connected to the TFT 93, it is possible to read out the electric charges even if the TFTs 43 of the normal pixels 41*a* in the same row are turned off and the charge accumulation operation is performed.

In the dose detection operation, under the control of the control unit 48, the gate driver 92 sequentially issues gate pulses g1, g2, g3, . . . , and gk (k<n) at a predetermined time interval so as to drive the TFTs 93 in the same row at a time. Thereby, the scanning lines 91 are sequentially activated on a row-by-row basis, and the TFTs 93 connected to the scanning lines 91 are turned on sequentially on a row-by-row basis. The time period for which the TFTs 93 are in an ON state is defined by a pulse width of the gate pulse. Upon elapse of the time period defined by the pulse width, the TFTs 93 return to an OFF state. The electric charges generated in the photoelectric converter 42 of each of the detection pixels 41*c* flow into the capacitor 49*b* of the integration amplifier 49 through the signal line 45 while the TFT 93 is in an ON state, irrespective of whether the TFT 43 is turned on or turned off. The electric charges of the detection pixel 41*c* accumulated in the integration amplifier 49 are outputted to the A/D 52 and converted into a dose signal by the A/D 52. The subsequent processing is the same as that in the first embodiment, and therefore the explanation thereof will be omitted.

The sampling period of the dose signal in this embodiment is a period of time from when the TFTs 93 are turned off and the accumulation of the electric charges in the detection pixels 41*c* is started to when the gate pulses are inputted to the TFTs 93 and the accumulated electric charges of the detection pixels 41*c* are outputted to the signal lines 45, in other words, the electric charge accumulation period of the detection pixels 41*c*. In this case, when the gate pulses g1, g2, g3, . . . , and gk are inputted to the TFTs 93 in each of the rows, the dose signals from all the detection pixels 41*c* are recorded in the memory 54.

According to this embodiment, in the case where the sampling period of the dose signal is changed as with the second embodiment, the time interval for inputting the gate pulses to the TFTs 93 in each of the rows may be changed so as to change the electric charge accumulation period of the detection pixels 41*c*.

Fourth Embodiment

Note that, in the sensor panel 90, while the TFTs 93 are turned off, the detection pixels 41*c* also can be used as the normal pixels 41*a*. Therefore, a plurality of the detection pixels 41*c* may be arranged in a lattice shape in the imaging area 40 as shown in FIG. 12, such that the TFT 93 of each of the detection pixels 41*c* can be selectively turned on/off. Additionally, the arrangement and the number of the detection pixels 41*c* may be different between the case of performing the judgment on whether or not the X-ray irradiation has been started and the case of performing the AEC. Namely, it is possible to select the detection pixels 41*c*, from which each of the irradiation start judging section 62 and the AEC section 63 obtains the dose signal, out of a plurality of the detection pixels 41*c* in the sensor panel 90. The selection of the detection pixels 41*c* is performed by the control unit 48.

Figure 13A:
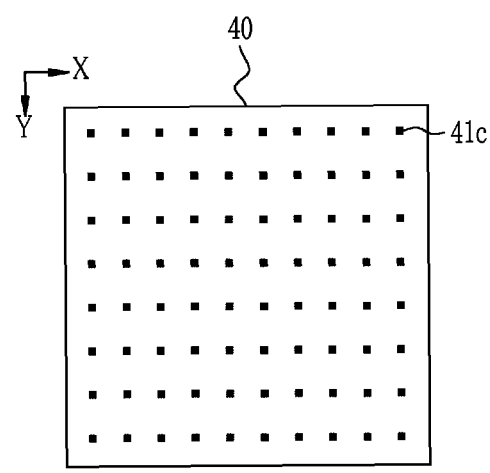
FIG. 13A is a view showing an example of selection of the detection pixels in the case of judging whether or not irradiation has been started.
Figure 13B:
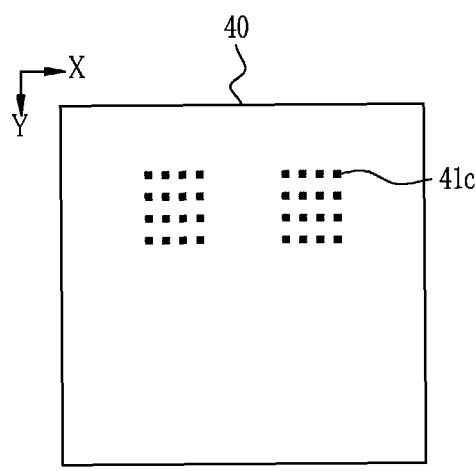
FIG. 13B is a view showing an example of selection of the detection pixels in the case of performing AEC.

In the case where the judgment on whether or not the X-ray irradiation has been started is performed, the detection pixels 41*c* uniformly distributed in the entire surface of the imaging area 40 as shown in FIG. 13A are selectively driven. In contrast, in the case where the AEC is performed, the detection pixels 41*c* densely arranged in the portions of the imaging area 40, which correspond to the lung fields as the dose measurement field in the chest radiography as shown in FIG. 13B, are selectively driven, for example. In FIG. 13A, in order to increase the S/N ratio of the dose signal at the time of judging whether or not the irradiation has been started, a plurality of the detection pixels 41*c* are arranged in one column. As the number of the detection pixels 41*c* arranged in one column is increased, an absolute value of the signal component of the dose signal is increased, and as a result, the S/N ratio of the dose signal is increased. Further, in FIG. 13B, the number of the detection pixels 41*c* per unit of area is made larger than that shown in FIG. 13A, such that the detection pixels 41*c* are densely arranged in particular portions. Since the arrangement and the number of the detection pixels are made different between the case of performing the judgment on whether or not the X-ray irradiation has been started and the case of performing the AEC as described above, it is possible to obtain the dose signal at a level appropriate for each of the intended purposes.

In the case where this embodiment is applied to the detection pixels 41*b* in each of which the TFT 43 thereof has a short between the source electrode and the drain electrode according to the first embodiment, the detection pixels 41*b* are uniformly distributed in the entire surface of the imaging area 40, and the detection pixels 41*b* are densely arranged in particular portions in the imaging area 40 corresponding to the dose measurement field in the AEC. Namely, it can be said that the arrangement of the dose detection pixels 41*c* shown in FIG. 13A and the arrangement of the dose detection pixels 41*c* shown in FIG. 13B are mixed in this embodiment. At the time of performing the judgment on whether or not the X-ray irradiation, the dose signals of the detection pixels 41*b* in the former case may be selectively read out from the memory 54 to the irradiation start judging section 62 so as to make a judgment. At the time of performing the AEC, the dose signals of the detection pixels 41*b* in the latter case may be selectively read out from the memory 54 to the AEC section 63 so as to perform the AEC.

Note that, as with the case of the gain of the integration amplifier 49 and the sampling period of the dose signal, irrespective of the judgment on whether or not the irradiation has been started and the AEC, in accordance with the tube current and the thickness of the object, the dose signal selectively read out from the memory 54 (which is in the case of the first embodiment) and the detection pixels 41c to be driven (which is in the case of the fourth embodiment) may be changed. For example, in the case where the tube current is lower than the standard value and in the case where the body part to be imaged is the chest, the abdomen, or the like that is relatively large and thick, the dose signal of the detection pixels 41b uniformly distributed in the entire surface of the imaging area 40 is selectively read out from the memory 54, or the detection pixels 41c uniformly distributed in the entire surface of the imaging area 40 are selectively driven. In contrast, in the case where the tube current is higher than the standard value and in the case where the body part to be imaged is the hand, the finger, or the like that is relatively small and thin, the dose signal of the detection pixels 41b arranged in the particular portions of the imaging area 40 is selectively read out from the memory 54, or the detection pixels 41c densely arranged in particular portions of the imaging area 40 are selectively driven.

In the above embodiments, when it is judged that the accumulated dose in the dose measurement field has reached the irradiation stop threshold value, the irradiation stop signal is outputted. Alternatively, the time at which the accumulated dose in the dose measurement field reaches the irradiation stop threshold value may be predicted, so as to transmit the irradiation stop signal to the source controller at the moment when the predicted time comes, or information of the predicted time itself may be transmitted to the source controller. In the latter case, the source controller measures the irradiation time, and stops the X-ray irradiation at the moment when the irradiation time reaches the predicted time.

Note that with taking advantage of the fact that electric current flowing through the bias line, which supplies the bias voltage to each of the pixels in the sensor panel, corresponds to the amount of the electric charges generated in each of the pixels, the electric current of the bias line connected to a particular pixel may be sampled so as to detect the dose. In this case, the pixel connected to the bias line of which electric current is sampled is considered as the dose detection sensor. In the similar manner, the leak current flowing from the pixel may be sampled so as to detect the dose. Also in this case, the pixel from which the leak current to be sampled flows is considered as the dose detection sensor. Additionally, another dose detection sensor, which has a structure different from that of the pixel and whose output is independent of that of the pixel, may be provided in the imaging area.

Although the console 14 and the electronic cassette 13 are separated from each other in the above embodiments, the console 14 may not be necessarily independent of the electronic cassette 13. The functions of the console 14 may be installed into the electronic cassette 13. Further, the console 14 may have part of the functions of the electronic cassette 13. Furthermore, in addition to the electronic cassette 13 and the console 14, an imaging control device for executing part of the functions of the console 14 for controlling the electronic cassette 13 may be provided between the electronic cassette 13 and the console 14.

In the above embodiments, the sensor panel is the TFT type. However, the sensor panel can be a CMOS type. Using the CMOS-type sensor panel has the following merit. The CMOS-type sensor panel can perform a so-called nondestructive readout operation, by which signal charges accumulated in each of the pixels are read out as a voltage signal through an amplifier provided in each of the pixels without flowing out to a signal line. Therefore, even in the accumulation operation, it is possible to detect the X-ray dose by selecting an arbitrary pixel in the imaging area and reading out the voltage signal from the pixel. Therefore, in the case of using the CMOS-type sensor panel, it is possible to use any of the normal pixels as the detection pixel without providing a pixel dedicated for the dose detection such as the above detection pixel.

Further, the present invention is applicable to not only an electronic cassette as a portable X-ray image detecting device but also an X-ray image detecting device installed on an imaging table. Furthermore, the present invention is applicable not only the case of imaging X-rays but also the case of imaging radiation such as gamma rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An x-ray radiation image detecting device comprising:
a sensor panel having an imaging area on which pixels are arranged, each of the pixels accumulating electric charges and outputting the electric charges to a signal line, the electric charges corresponding to a dose of x-ray radiation having been irradiated from an x-ray radiation source and having passed through an object;
a dose detection sensor for outputting a dose signal corresponding to the dose of x-ray radiation;
an amplifier for amplifying the dose signal;
an irradiation start judging section for judging whether or not x-ray radiation irradiation has been started based on the dose signal amplified by the amplifier;
an AEC section for judging whether or not an accumulated dose of x-ray radiation has reached a target dose based on the dose signal amplified by the amplifier; and
a control unit for setting a gain of the amplifier at the time of judging whether or not x-ray radiation irradiation has been started by the irradiation start judging section lower than a gain of the amplifier at the time of judging whether or not the accumulated dose of x-ray radiation has reached the target dose by the AEC section; and
wherein the control unit sets a sampling period of the dose signal at the time of judging whether or not x-ray radiation irradiation has been started by the irradiation start judging section shorter than a sampling period of the dose signal at the time of judging whether or not the accumulated dose of x-ray radiation has reached the target dose by the AEC section.

2. The x-ray radiation image detecting device according to claim 1, wherein the control unit changes the gain in accordance with at least one of tube current set in a source controller and a thickness of the object.

3. The x-ray radiation image detecting device according to claim 1, wherein the control unit changes a sampling period of the dose signal in accordance with at least one of tube current set in a source controller and a thickness of the object.

4. The x-ray radiation image detecting device according to claim 1, wherein a plurality of the dose detection sensors are arranged in the imaging area.

5. The x-ray radiation image detecting device according to claim 4, wherein the dose detection sensors, from which each of the irradiation start judging section and the AEC section obtains the dose signal, are selected from a plurality of the dose detection sensors.

6. The x-ray radiation image detecting device according to claim 5, wherein
the dose detection sensors distributed in an entire surface of the imaging area are selected, and based on the dose signals from the selected dose detection sensors, the irradiation start judging section judges whether or not x-ray radiation irradiation has been started, and
the dose detection sensors arranged in a portion of the imaging area corresponding to a region of interest which is the most remarkable in diagnosis are selected, and based on the dose signals from the selected dose detection sensors, the AEC section judges whether or not the accumulated dose of x-ray radiation has reached the target dose.

7. The x-ray radiation image detecting device according to claim 5, wherein the dose detection sensors to be used for the judgment are selected in accordance with at least one of tube current set in a source controller and a thickness of the object.

8. The x-ray radiation image detecting device according to claim 4, wherein the dose detection sensors are equivalent to part of the pixels.

9. The x-ray radiation image detecting device according to claim 8, wherein
the pixels are normal pixels each for accumulating signal charges upon receiving x-ray radiation and outputting the signal charges to the signal line in response to actuation of a switching element, and detection pixels directly connected to the signal line by a short-circuit line or directly connected to the signal line without the switching element, and
each of the detection pixels is used as the dose detection sensor.

10. The x-ray radiation image detecting device according to claim 8, wherein
the pixels are normal pixels each for accumulating signal charges upon receiving x-ray radiation and outputting the signal charges to the signal line in response to actuation of a switching element, and detection pixels each of which is driven separately from the normal pixels and provided with a switching element, and
each of the detection pixels is used as the dose detection sensor.

11. The x-ray radiation image detecting device according to claim 1, wherein the sensor panel is an electronic cassette contained in a portable housing.

* * * * *